Nov. 10, 1931. V. GROSHENS Plant Pat. 5
ROSE
Filed April 20, 1931
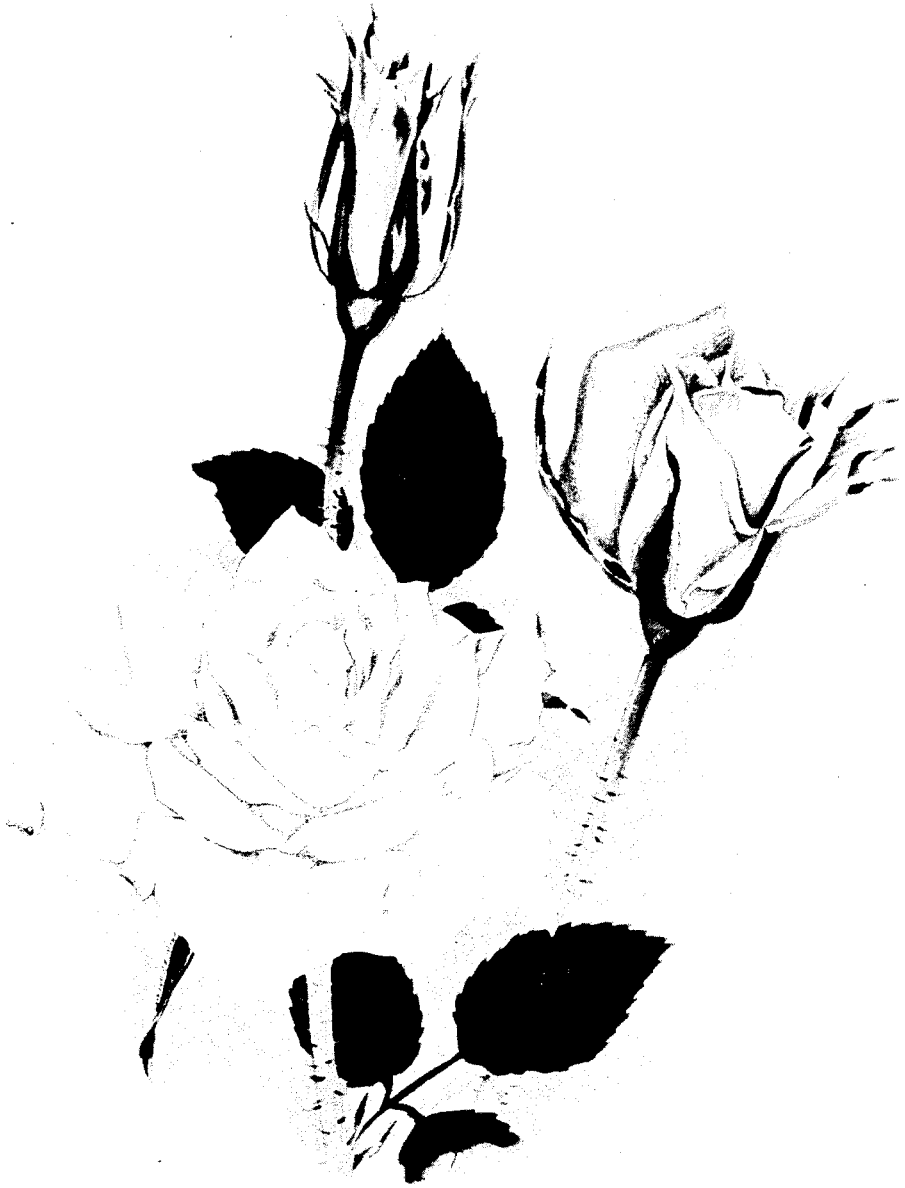
WITNESSES
John A. Weidler
William Bree, Jr.
DISCOVERER:
Victor Groshens,
BY Fraley & Paul
ATTORNEYS.

Patented Nov. 10, 1931

Plant Pat. 5

UNITED STATES PATENT OFFICE

VICTOR GROSHENS, OF ROSLYN, PENNSYLVANIA

ROSE

Application filed April 20, 1931. Serial No. 531,456.

My invention or discovery relates to roses, and the distinct and new variety of rose which I have reproduced, while most closely resembling the variety from which it has sported, known as "Talisman", has certain characteristics, especially as to color, proportions, and the formation of the bloom and calyx by which it may be readily distinguished from its parent "Talisman" stock.

The new variety of rose which forms the subject of my discovery or invention was propagated by making cuttings of side shoots of the species called "Talisman" which cuttings were rooted. Upon one shoot on one of these cuttings, a sport appeared. Whereupon additional cuttings were made from the original sport which were rooted and cultivated, and the new variety thereafter became permanently fixed.

"Talisman" is a variety of the major class known as hybrid-tea roses and possesses free blooming qualities which have made it commercially popular. When the bud of "Talisman" begins to open, the outside of the petals are characterized by a predominance of yellow color, at times bordering on orange and gold, and especially prominent at the base of the petals. As the bud further expands and the inside of the petals becomes visible, a combination of pink and yellow colors in about equal proportions is seen. The coloring of the reverse side or outside of the petals then commences to fade, and when the flower has fully developed the yellow color fills the inside at the center and merges into varying shades of pink most prominent near the points of the petals. At this stage there is very little, if any, pink visible on the reverse side of the petals which are almost colorless. The petals are sharply pointed and are of delicate texture with the veins resembling fine threads; the calyx is of unusual length and pointedness.

My rose possesses substantially the same blooming qualities and habits of growth as "Talisman", but has certain marked distinguishing characteristics as follows:

The predominating color of the bloom of my rose is known commercially as "rose carthame"; the long tapering bud rises from a stroutian base having a relatively small spot of yellow sometimes hardly visible upon a casual inspection; the petals expand into "rose carthame", tipped with magenta in the deeper shading; in contrast with "Talisman" the reverse sides or outsides of the petals in the full bloom are richly colored with such "rose carthame"; the calyx is even longer than that of "Talisman"; as to texture the petals have coarser and more prominent veins.

Furthermore, when the bloom of my rose fades and the petals drop, the brilliant pink fades out into a lavender tinting. The leaf growth is of a dull rather than the glossy green which characterizes "Talisman".

The coloring and proportions of the leaf growth, the stem, the petals and the calyx are accurately reproduced in the accompanying water-colored drawing, which shows the rose in various stages of development.

Having thus described my invention, I claim:

The rose as shown and described, characterized by petals having on the major portion of both sides the color of rose carthame.

In testimony whereof, I have hereunto signed my name at Philadelphia, Pennsylvania, this 15th day of April, 1931.

VICTOR GROSHENS.